United States Patent
Oni et al.

[19]

[11] Patent Number: 5,803,924
[45] Date of Patent: Sep. 8, 1998

[54] EXTERNAL FIXATOR

[75] Inventors: Olusola Olumide Akindele Oni, Leicester; Richard Mark Gale; John Stephen Batchelor, both of Warwickshire, all of United Kingdom

[73] Assignee: Hi-Shear Fastners Europe Limited, Butlers Leap Rugby, United Kingdom

[21] Appl. No.: 592,367

[22] PCT Filed: Aug. 5, 1994

[86] PCT No.: PCT/GB94/01725

§ 371 Date: Apr. 12, 1996

§ 102(e) Date: Apr. 12, 1996

[87] PCT Pub. No.: WO95/04504

PCT Pub. Date: Feb. 16, 1995

[30] Foreign Application Priority Data

Aug. 5, 1993 [GB] United Kingdom .................... 9316263

[51] Int. Cl.$^6$ .................................................. A61B 17/56
[52] U.S. Cl. .................................. 606/54; 606/57; 606/59
[58] Field of Search ................................... 606/54, 57, 58, 606/59, 53

[56] References Cited

U.S. PATENT DOCUMENTS

| | | | |
|---|---|---|---|
| 2,398,915 | 4/1946 | Bell | 606/59 |
| 4,448,482 | 5/1984 | Lathlaen | 350/96.21 |
| 5,320,622 | 6/1994 | Faccioli et al. | 606/58 |

FOREIGN PATENT DOCUMENTS

| | | |
|---|---|---|
| A-24503/92 | 3/1993 | Australia . |
| 0011258 B1 | 5/1980 | European Pat. Off. . |
| 0099289 | 1/1984 | European Pat. Off. . |
| 0298100 B1 | 1/1989 | European Pat. Off. . |
| 0298400 A1 | 1/1989 | European Pat. Off. . |
| 0424734 A1 | 5/1991 | European Pat. Off. . |
| 2499400 | 2/1981 | France . |
| 3822740 A1 | 1/1989 | Germany . |
| 2146533 | 4/1985 | United Kingdom . |
| 2154143 | 9/1985 | United Kingdom . |
| 2154144 | 9/1985 | United Kingdom . |
| 2258155 | 2/1993 | United Kingdom . |
| WO 91/16860 | 11/1991 | WIPO . |
| WO 94/02078 | 2/1994 | WIPO . |

OTHER PUBLICATIONS

Leaflet on Orthofix® Modulsystem showing prior art systems.

Leaflet on Isodyn® External Fixator showing prior art systems.

Primary Examiner—Michael Buiz
Assistant Examiner—Julian W. Woo
Attorney, Agent, or Firm—Ostrolenk, Faber, Gerb & Soffen, L.L.P.

[57] ABSTRACT

An external fixator comprises transfixing pins having a flange which abuts against the bone surface to distribute stress along the length of the threaded portion extending into the bone. The pins are mounted in elastomeric bushes in an outrigger to allow limited movement at the outrigger. The outrigger comprises two clamps which are connected through an elastomeric bush allowing a small degree of axial bending and rotational movement of the clamps relative to one another. The arrangement reduces loosening of the pins in the bone and allows beneficial relative movement of the fractured bone portions near the fracture site.

14 Claims, 6 Drawing Sheets

FIG. 5

EXTERNAL FIXATOR

The present invention relates to an external fixator.

Fractures of bone heal by the formation, at the site of the fracture, of a bone-like reparative tissue called callus. Bone fracture treatment attempts to hold the bone fragments in anatomical alignment while the natural process of healing is taking place. Fracture surgeons employ various methods of operative treatment such as the use of plates and screws, intra-medullary nails and external fixators to hold fracture fragments in normal alignment.

External fixation refers to the rigid anchorage of bone fragments to an external device (an outrigger) such as a metal bar, via the medium of transfixing pins. By these means, the fractured bone may be kept relatively immobile while the fracture heals, allowing use of the limb etc.

Typically, a single or unilateral outrigger, essentially a metal splint, is located outside the body, and bone fragments are fastened to it through the medium of pins. The outrigger is usually a rigid metal bar incorporating fixed or sliding pin-holding clamps. With this type of fixator, it is difficult to maneuver bone fragments into new positions once pins have been inserted. Furthermore, pin sites are usually limited to two or three per fracture fragment.

Modular fixators have been developed. In this variety, one or more outrigger members are linked together like a piece of scaffolding by way of special clamps. However, although the modular fixator is more versatile in its applicability, it is often less stable than the rigid fixator with consequent risk of fracture displacement and mal-alignment. Too much movement at the fracture site is deleterious to healing, often resulting in non-union or delayed union.

On the other hand, the rigid fixator prevents the micro-movement at the fracture site which is necessary for normal healing. The result is diminished callus formation and, as a consequence, delayed union and non-union. Hence, rigid fixators have been modified to allow some degree of axial movement at the fracture site, i.e. in the direction of the bone axis. Simple telescoping devices are the usual methods but the current designs have been shown by several workers to be unreliable in performing the function.

Pin loosening is a common complication of external fixation of fractures. The aetiology is not entirely clear but may be due to problems with pin anchorage in bone. According to some workers a less than secure anchorage causes bone resorption. It has been suggested that pin anchorage in bone may be improved by pin design but this has not been supported by results from pull-out tests. Other workers have suggested radial pre-load techniques, in which the pin is fitted into an undersized hole, and a pre-load technique in which the pin is bent resiliently before clamping to the external frame, but these methods do not prevent bone resorption at the pin-bone interface.

Loosening may also be due to mechanical failure at the pin-bone interface. Excessive stresses generated in the bone by axial and bending forces may cause local bone failure. Stresses generated at the pin-bone interface may be reduced by increasing the stiffness of the pins. In practice this is done by using large diameter pins or by increasing the number of pins. However, these methods do not prevent pin loosening. Furthermore, there is a limit to the size of pins, otherwise fracture of the bone will occur at the pin site.

Conical pins have been used, but it appears from theoretical calculations that these may increase shear stress and stresses at the pin-bone interface.

One aim of the present invention is to provide an external fixator which will allow a controlled degree of micro-movement at the fracture site. Micro-movement (generally less than 0.5 mm) is intended to simulate the movement experienced within unfractured bone.

Another aim of the invention is to provide a transfixing pin which will be held securely in the bone.

A first aspect of the invention provides an outrigger for an external fixator, the outrigger comprising first and second members for attachment to respective bone portions, and connecting means connecting the first and second members in an axial direction, wherein the connecting means allows a limited degree of axial and bending movement of one member relative to the other.

Preferably, the connector means also allows a limited degree of relative rotation of the members about the axial direction.

Very preferably the degree of movement reflects closely the micro-movement of the bone or callus cartilage.

Preferably the connecting means comprises an elastomeric member. Preferably the elastomer has a Poisson ratio of about 0.3 and a modulus of elasticity to match the callus cartilage.

Preferably the elastomer is sandwiched between two connector members which are adjustably connected respectively to the first and second members. Preferably the connection is by a ball and socket joint which can be fixed in position to allow a high degree of relative movement of the first and second members when attaching the outrigger to the bone and facilitating alignment of the bone fragments.

A second aspect of the invention provides an outrigger for an external fixator, the outrigger comprising first and second members for attachment to respective bone portions, and connecting means connecting the first and second members, wherein the connecting means comprise an elastomeric member which allows a limited degree of movement between the members in the axial direction.

A third aspect of the invention provides a transfixing pin for an external fixator, the pin comprising a shank and a threaded portion at an end of the shank for screwing into the bone, wherein flange means is provided on the shank for mating against the surface of the bone where the threaded portion enters the bone.

It is believed that by providing a flange which mates against the bone surface, tensile forces are developed along the length of the threaded portion in the bone and these serve to reduce the concentration of stress at the point of entry into the bone.

A fourth aspect of the invention provides an external fixator comprising an outrigger, and a plurality of transfixing pins which are screwed at one end into the bone and mounted on the outrigger at their other end, wherein means mounting one or more of the pins on the outrigger allow a limited degree of movement of the pin or pins relative to the outrigger.

It is believed that this arrangement will reduce the stress at the pin-bone interface as the movement of adjacent pins caused by flexing of the bone portion can be reflected in movement at the outrigger.

Other aspects and preferred features of the invention will be apparent from the following description and the accompanying claims.

The invention will be further described by way of example with reference to the accompanying drawings, in which:

FIG. 12b is an enlarged view of the connector of FIG. 12a.

Figure 1:
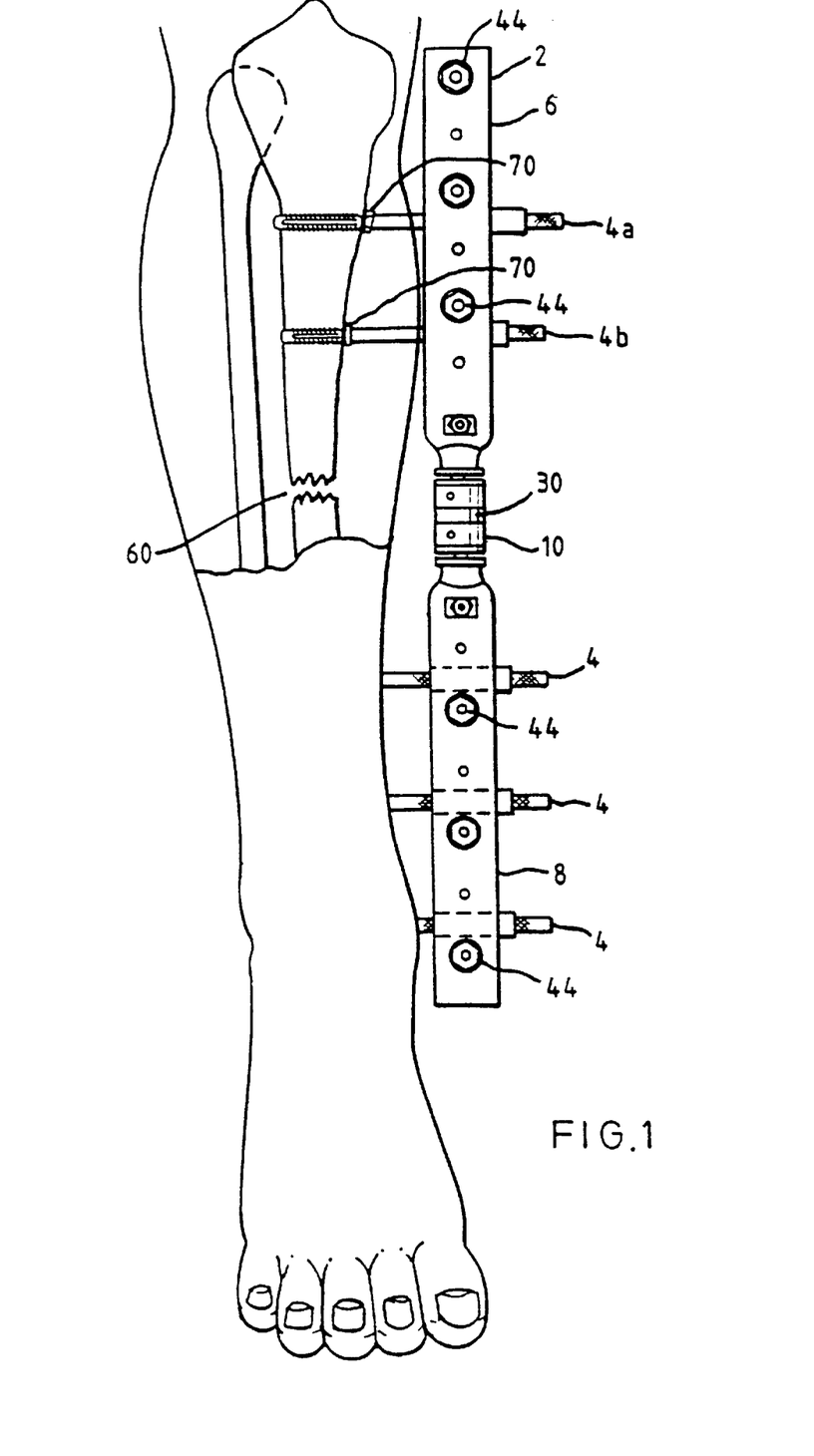
FIG. 1 shows an external fixator according to the invention, shown attached to a fractured tibial shaft.

FIG. 1 shows an external fixator comprising an outrigger 2 and transfixing pins 4. The outrigger 2 is formed by first and second elongate clamp members 6, 8 which are held together by a connector means 10. Each clamp has a body part with opposite ends and a length dimension between said ends. The clamps 6, 8 are clamped about the free ends of the transfixing pins 4.

The connector 10 (see FIG. 3) forms a particular feature of this invention and comprises first and second ball ends 12, 14 which are received in sockets 16, 18 in the clamps 6, 8 to form ball and socket joints. The ball ends 12, 14 are formed on oppositely threaded shafts 20, 22 which are screwed into a central composite cylinder 24.

Figure 3:
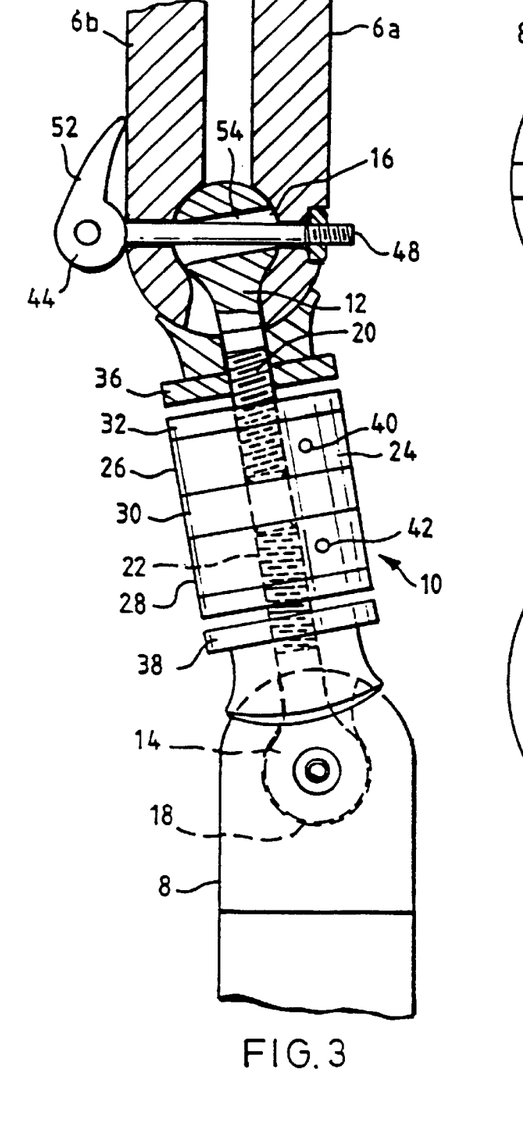
FIG. 3 is a detailed view, partly cut-away, showing a connector of the fixator of FIG. 1.

Composite cylinder 24 has metal outer cylinders 26, 28, which are threaded to receive the shafts 20, 22, and bonded to a circular disc-shaped elastomeric pad 30. Lock-nuts 32, 34 secure the shafts 20, 22 in position in the cylinders 26, 28. For additional security, the cylinders 26, 28 are split radially and locking screws 40, 42 clamp the cylinders about the shafts 20, 22. Lock-nuts 36, 38 are shaped to mate with spherically formed with ends of the members 6, 8 and distribute the load from the members 6, 8 to the connector 10.

The clamps 6, 8 are formed in two halves 6a, 6b; 8a, 8b. They are clamped about the ball ends 12, 14 by quick release clamping pins 44. The pins 44, comprise a shaft 48 threaded at one end to carry an adjustment nut 50 and fitted with an over-center cam 52 at the other end. The shafts 48 pass through an eye 54 in the ball ends. Thus, referring to FIG. 3, it can be seen that there is considerable freedom for adjusting the orientation of the clamps 6, 8 relative to one another about the connector 10.

The elastomeric pad 30 functions as a shock absorber allowing micro-movement between the clamp members 6, 8 and hence between the respective bone portions 56, 58 of the fractured bone shaft. It is particularly preferred that the pad 30 allow movement along the axial direction of the bone at the fracture site, i.e. compression and extension. By micro-movement we mean a degree of movement which is similar to the movement experienced by the bone, and typically this will be less than about 0.5 mm.

The material and shape of the disc 30 are selected to control the amount of micro-movement allowed. This may depend on the fractured bone under repair, but conveniently the material has similar elastic properties to the callus cartilage, in particular a Poisson ratio of about 0.3.

A suitable material for the elastomeric pad, which will be embedded in the midsection, is a material called Microvon developed by Dunlop. The mechanical properties of this material are similar to that of bone. It has a Poisson ratio (i.e. measure of the ability of a material to conserve volume when loaded in one direction) of 0.3 to 0.5 which is comparable to that of bone and cartilage. It is a "cellular solid" with low density which permits the design of light and stiff structures. Its stiffness makes it an ideal "cushing" material and its low strength and large compressive strains allow it to absorb energy. End conditions such as bonding and lubrication do not affect its stress-strain properties.

The elastomeric pad 30 allows relative axial movement of the clamps, 6, 8; bending movement and also rotation about the axial line of the clamps. Thus the assembly is able to emulate the range of movement which will be experienced by the bone at the fracture region in normal use. It will be appreciated that the movement occurring at the fracture site 60 may not reflect precisely the natural flexing of the bone because it is controlled by the pad 30 which is displaced laterally. However, it is believed that improved healing performance can be obtained by providing an elastomeric pad which will allow a very small amount of movement (micro-movement) in the axial direction, as well as bending and torsional movement.

The connector 10 allows for distraction and compaction procedures to be carried out. The lock nuts 32, 34 and locking screws 40, 42 are released and the cylinder 24 rotated to move the ball ends 12, 14, and hence the clamps 6, 8 towards or away from each other (the shafts 20, 22 being of opposite thread).

Figures 6, 6A:
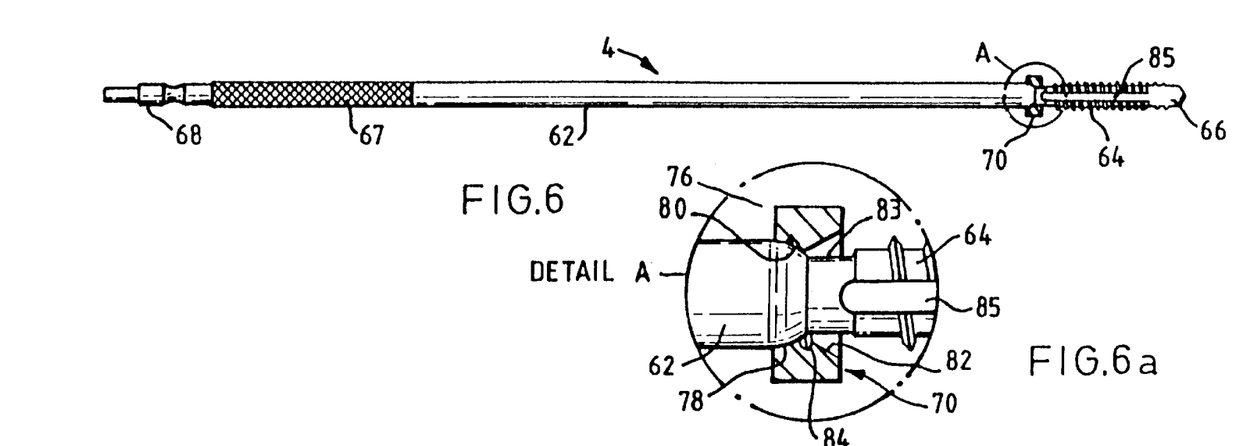
FIG. 6 shows a transfixing pin according to the invention.
FIG. 6a is a detailed view showing a self-aligning collar on the transfixing pin of FIG. 6.

Referring to FIG. 6, the transfixing pins 4 will be described in more detail.

The pins 4 are designed to perform simultaneously the actions of drilling and screwing into the bone, however these procedures can be performed separately.

The pins 4 comprise a shank 62 having a self-tapping threaded portion 64 at one end, with a drill tip 66. The other end of the shank 62 has a knurled portion 67 for gripping in a clamp 6, 8, and has a fitting 68 for attachment to a drill or tommy bar for when the pin is to be driven into the bone fragment. The pin will be dimensioned to suit various applications. Typically the thread portion is 25 mm to 50 mm, and the shank diameter 5.0 mm.

Figure 2A:
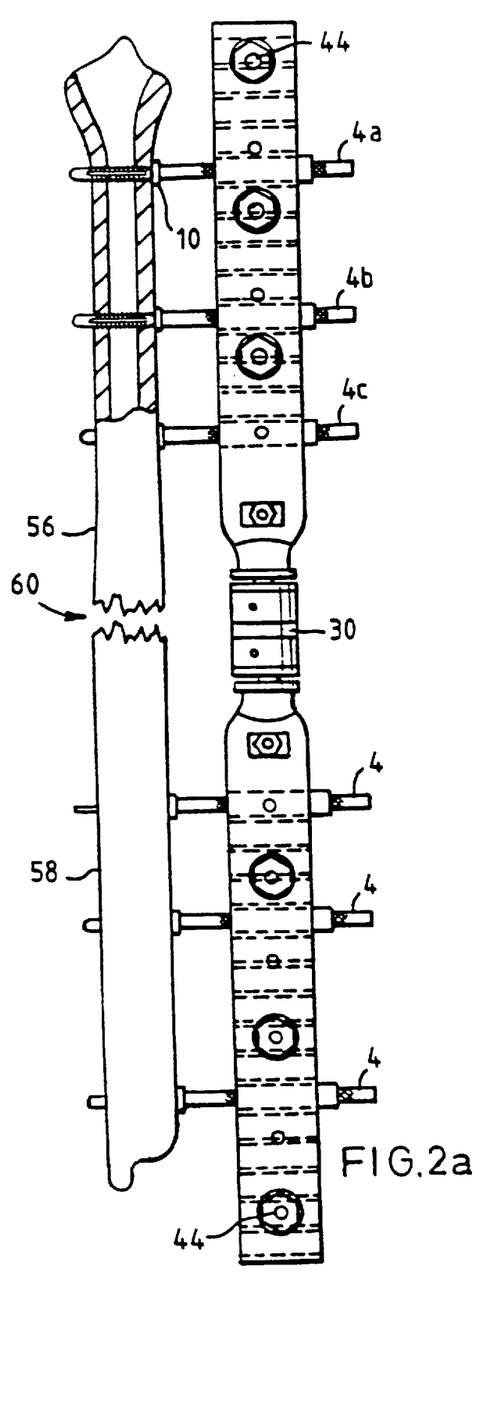
FIG. 2a shows the fixator of FIG. 1, partly cut-away.
Figure 2B:
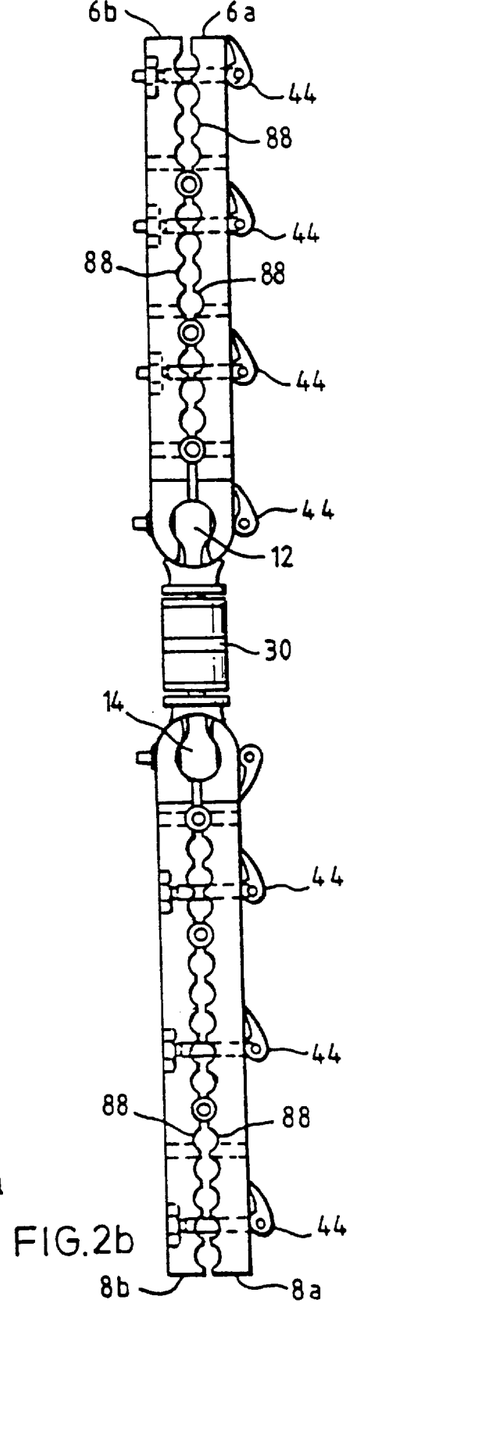
FIG. 2b shows a side view of the fixator of FIG. 1.

In accordance with the invention, a flange 70 is provided at the inner end of the threaded portion to abut the surface of the bone (see FIGS. 1 and 2a). The flange 70 may be formed by a shoulder 72 on the shank as at FIG. 7c, by an integral collar 74 as at FIG. 7a, or as a self-aligning collar 76 as at FIGS. 6 and 7b.

Preferably the flange is 1 to 3 mm wide, and preferably about 2 mm measured in the radial direction from the circumferential plane of the pin thread.

Figure 7A:
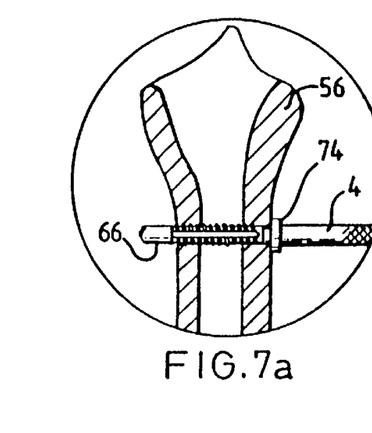
FIGS. 7a to 7c show modifications of the pin of FIG. 6.
Figure 7B:
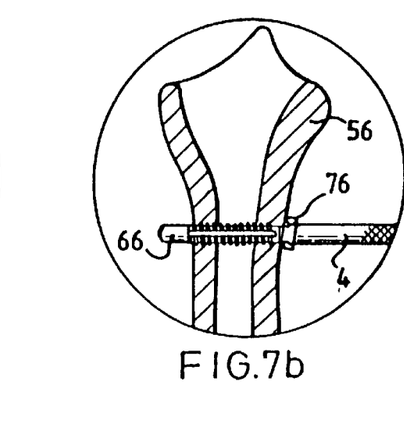
Figure 7C:
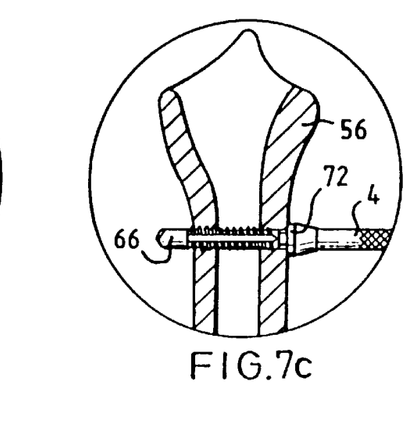

In many areas of the bone the pin 6 will be inserted substantially perpendicular to the bone surface and so arrangements such as FIGS. 7a and 7c are suitable. A self-aligning collar is used in other applications. As seen in the detail "A" of FIG. 6a, the self-aligning collar has a cup-shaped surface 78 which bears on a rounded shoulder 80 on the shank 62. The collar has a conical throat 82 facing the thread to allow it to swivel on the shoulder 80, and carries a thread 84 to allow it to be screwed over the threaded end 64 during assembly of the pin.

An undercut 83 is formed at the inner end of the threaded portion 64 to avoid any localized stress at the point of entry of the pin into the bone.

The flange 70 may be formed by a lock-nut which is screwed down the pin 4 to bear against the bone surface or cortex after the pin 4 has been screwed into the bone.

In use, the pin is screwed into the bone until the flange 70 abuts tightly against the bone surface, so as to distribute the "stress" of the fixing along the length of the threaded portion 64 in the bone.

Overtightening will strip the "thread" formed in the bone which typically undergoes plastic deformation. Thus, the screw is tightened by means of a torque wrench to a preferred pre-determined torque. The torque can be determined from experimentation by the manufacturer and this information is supplied to the operating surgeon.

A groove 85 is provided in the threaded portion 64 to allow bone dust to escape as the bone is being drilled.

The knurled portion 67 is fitted with an elastomeric sleeve 86 (FIG. 4) and this is clamped between recesses 88 formed in the cooperating halves 6a, 6b; 8a, 8b of the clamp members 6, 8. The sleeve 86 is preferably of the same material as the disc 30.

A row of closely spaced recesses 88 is provided in each half of the clamps 6, 8 to simplify the choice of position when fixing the pins 4 in the bone.

The clamp halves 6a, 6b; 8a, 8b are clamped about the pins 4 by quick-release clamps 44.

Figure 4:
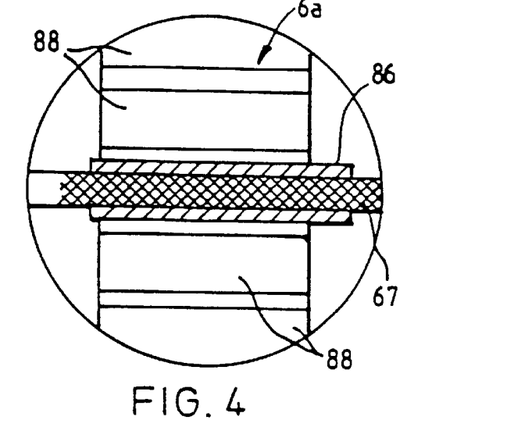
FIG. 4 is a detailed view showing the mounting of a transfixing pin in the outrigger of the fixator of FIG. 1.
Figure 5:
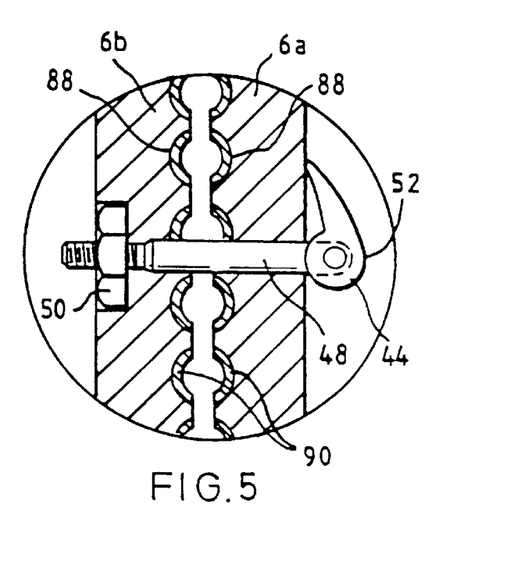
FIG. 5 shows in a detailed view a modification of FIG. 1.

In the modification shown in FIG. 4, the recesses 88 are lined with elastomeric material 90, so that sleeve 86 is not required on the pin 4.

The elastomeric sleeve 86 or lining 90 allows adjacent pins 4a, 4b in a bone portion to move relative to one another, and fixing of the bone portion can be taken up by the movement of the pins at the clamp. Thus, it is believed that there will be less stress applied to the pin-bone interface.

Figure 8A:
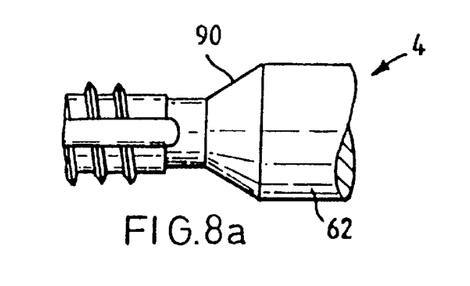
FIGS. 8a and 8b show further modifications of the pin of FIG. 6.
Figure 8B:
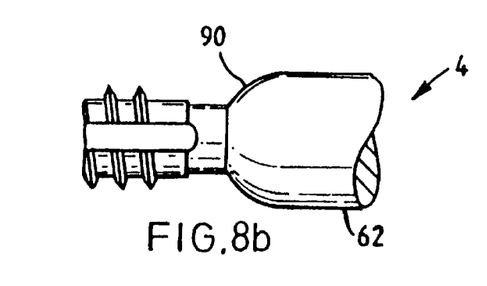

FIGS. 8a and 8b show a modified pin in which the flange 70 is formed by a conical shoulder 90 on the shank 62. The conical shoulder may be a plane sided cone as in FIG. 8a, or an arcuate shape as in FIG. 8b. The surface of the bone is recessed, by pre-drilling, to snugly receive conical shoulder 90.

In use, a first pin 4a is screwed into the bone 56 to a predetermined torque so that the flange 70 abuts tightly against the cortex.

An outer sleeve may be used to protect soft tissue from the threaded end 64 while the pin is being fixed in place. A template or rule is then used to position the next pin 4b to ensure that the pins 4 align with respective recesses 80 in the clamp member 6. The procedure is then repeated for the remaining pins. With the clamp members 6, 8 clamped about the ends of the pins 4, the relative positions of the clamp members are adjusted at the connector 10 to align the bone fragments, and the clamps 44 at the ball and socket joints and then tightened. The connector 10 is arranged to align approximately with the fracture site 60. Typically the bone fragments will be aligned with a small gap between them. When weight is applied to the limb, the pad 30 will compress to allow the fragments to come together.

The limb is used with the external fixator in place, the elastomeric pad 30 allowing controlled axial micromovement at the fracture site.

It will be appreciated that two or more fixators may be used for repairing a fractured bone.

Preferably parts may be of stainless steel or titanium and the clamps 6, 8 of lightweight metal, such as aluminium.

The embodiment of FIGS. 9 and 10 will now be described. The construction is generally similar to the construction of the embodiment of FIGS. 1 to 3 and like reference numerals will be used where appropriate.

In this embodiment, one of the clamp halves 6a, 8a is divided to provide a separate clamping portion 6c, 8c for clamping the free ends of the transfixing pins 4 to the other clamp half 6b, 8b. This makes it easier to offer the clamp half 6b, 8b, up to the pins 4 after they have been screwed into the bone fragment.

Figure 9:
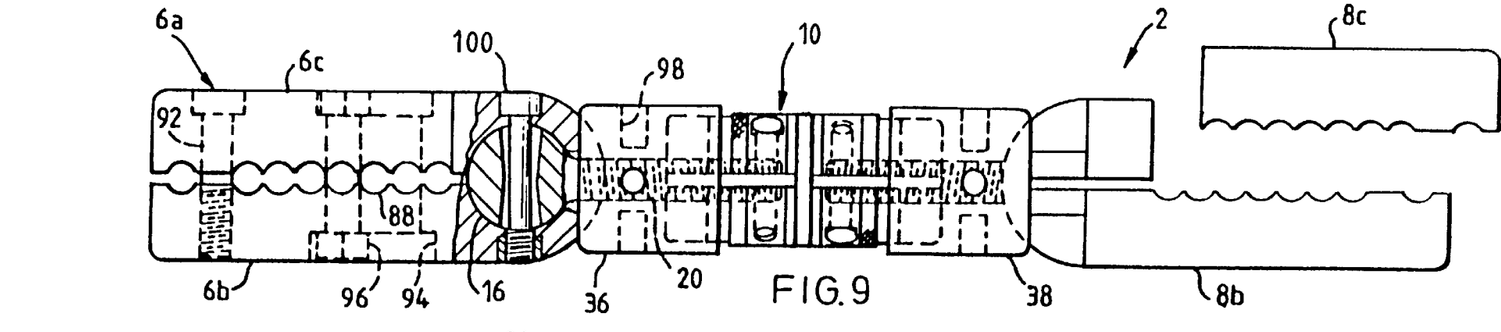
FIG. 9 shows a side view of a second embodiment of a fixator according to the invention.
Figure 10:
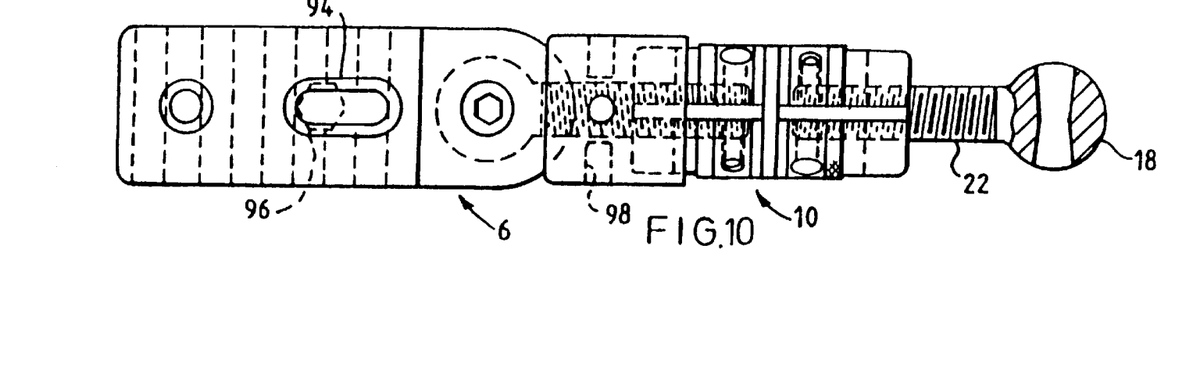
FIG. 10 shows a front view of the fixator of FIG. 10.

The clamp portions 6c, 8c, are attached to the clamp halves 6b, 8b by a screw 92 which screws into the clamp half 6b, 8b as shown in FIG. 9. An elongate slot 94 is provided for clamping with a nut and bolt 96. The elongate slot 94 allows more pin recesses 88 to be provided along the length of the clamps, the nut and bolt 96 being positioned appropriate in the slot 94 to avoid the pin.

The lock nuts 36, 38 are threaded on the ball shafts 20, 22 and recesses 98 are provided for tightening with a tommy bar to lock the nuts 36, 38 against the ends of the clamp halves 6, 8 to further secure the ends 16, 18. A nut and bolt 100 is used to clamp the clamp halves 6a, 6b on the ball end 16, and similarly for the other clamp halves 8a, 8b.

As with the embodiment of FIGS. 1 and 2, an elastomeric pad 30 is bonded to split, threaded cylinders 28, 26, which are screwed on the appropriately threaded shafts 20, 22 and locked in position by tightening on locking screws to clamp the cylinders 28, 26 on the shafts 20, 22.

In this embodiment, the transfixing pins 4 are clamped directly between the clamp halves 6b, 6c; 8b, 8c, without interposing an elastomeric sleeve.

Figure 11:
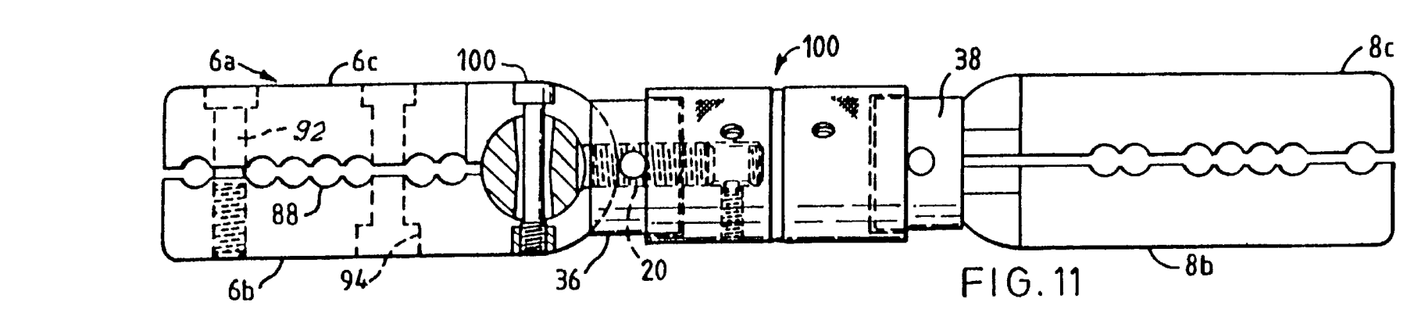
FIG. 11 shows a side view of a third embodiment of a fixator according to the invention.
Figure 12A:
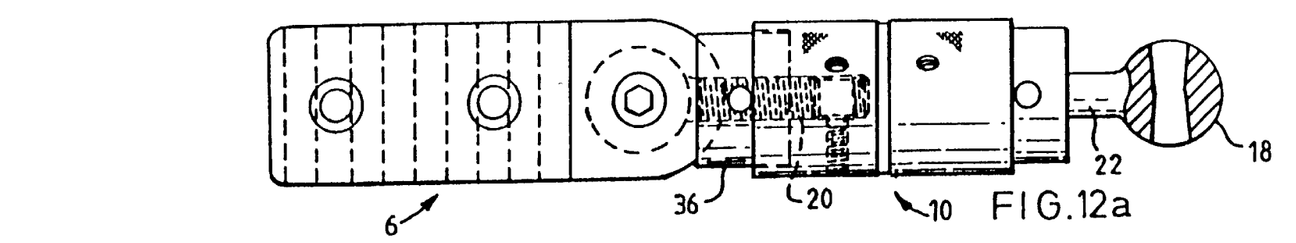
FIG. 12a shows a front view of the fixator of FIG. 11.
Figure 12B:
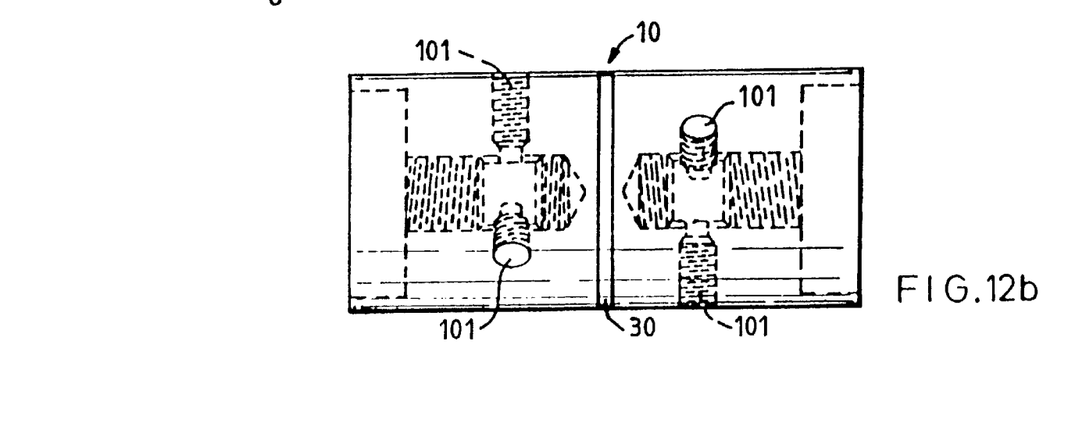

The embodiment of FIGS. 11, 12a, and 12b will now be described. The construction is generally similar to the construction of the embodiment of FIGS. 1 to 3 and like reference numerals will be used where appropriate.

In this embodiment, one of the clamp halves 6a, 8a is divided to provide a separate clamping portion 6c, 8c for clamping the free ends of the transfixing pins 4 to the other clamp half 6b, 8b. This makes it easier to offer the clamp half 6b, 8b, up to the pins 4 after they have been screwed into the bone fragment.

The clamp portions 6c, 8c, are attached to the clamp halves 6b, 8b by a screw 92 which screws into the clamp half 6b, 8b as shown in FIG. 9. A slot 94 is provided for clamping with a nut and bolt 96. Although not shown, the slot 94 could be elongate, to allow more pin recesses 88 to be provided along the length of the clamps, the nut and bolt 96 being positioned appropriate in the slot 94 to avoid the pin.

The lock nuts 36, 38 are threaded on the ball shafts 20, 22 and recesses 98 are provided for tightening with a tommy bar to lock the nuts 36, 38 against the ends of the clamp halves 6, 8 to further secure the ends 16, 18. A nut and bolt 100 is used to clamp the clamp halves 6a, 6b on the ball end 16, and similarly for the other clamp halves 8a, 8b.

In the connector 10, an elastomeric pad 30 is bonded between two internally threaded cylinders 28, 26 which are screwed on to the appropriately threaded shafts 20, 22 and locked in position by three locking screws 101 per cylinder. The locking screws are equally spaced at 120° intervals so that access to two screws is always available from one side. The threaded shafts are undercut so that the locking screws can clamp onto a flat surface. The undercut on the threaded shaft will also allow maximum and minimumn length adjustment of the fixator.

In this embodiment, the transfixing pins 4 are clamped directly between the clamp halves 6b, 6c; 8b, 8c, without interposing an elastomeric sleeve.

In an alternative embodiment (not illustrated), the elastomeric pad 30 is omitted, to provide a rigid connector.

We claim:

1. An outrigger for an external fixator, the outrigger comprising first and second pin holding members for attachment to respective bone portions, and connecting means connecting the first and second pin holding members in generally axial alignment, the connecting means comprising first and second connector members which are each attached to a respective one of the first and second pin holding members by a ball and socket connection, the first and second connector members being joined together only by a pad of compressible material allowing limited relative movement of the first and second connector members.

2. An outrigger as claimed in claim 1, wherein the pad of material has a Poisson ratio of about 0.3.

3. An outrigger as claimed in claim 1, wherein the limited relative movement comprises an axial movement of less than 0.5 mm.

4. An outrigger as claimed in claim 1, wherein the degree of limited relative movement is similar to the compressive axial movement of bone across the fracture site.

5. An outrigger as claimed in claim 1, wherein the connector means allows a limited degree of relative rotation of the first and second pin holding members about the axial direction.

6. An outrigger as claimed in claim 1, wherein the connecting means comprises an elastomeric member.

7. An outrigger as claimed in claim 1, wherein the ball and socket connections each comprise a ball end provided on the respective connector member and a socket provided on the respective pin holding member.

8. An outrigger as claimed in claim 7, wherein each ball end is provided on a threaded rod which is screwed into the respective connector member, and a clamping collar is threadedly mounted on each rod for clamping each socket in a fixed position on the respective ball end.

9. An outrigger as claimed in claim 7, wherein each pin holding member comprises first and second clamping parts each having a plurality of parallel pin receiving grooves in a surface thereof, and further comprising clamping means to clamp the clamping parts together about one or more pins with said surfaces facing each other and said pins located in said grooves.

10. In combination, an outrigger for an external fixator, and a plurality of transfixing pins, the outrigger comprising first and second pin holding members for attachment to the respective bone portions by means of said pins, each of said pin holding members having a body part with opposite ends and a length dimension extending between said ends, and a connecting means connecting the first and second pin holding members in end-to-end relationship, the connecting means including means for adjusting the relative position and orientation of said pin holding members, and said pin holding members each including clamping means for clamping a free end of a transfixing pin in said pin holding member, said pin holding members being spaced apart in said length direction and said transfixing pins extending transversely of said length direction, and the transfixing pins each comprising a shank and a threaded portion at an end of the shank for screwing into a said bone portion, wherein a flange is provided on the shank for bearing against the surface of the bone where the threaded portion enters the bone.

11. An outrigger as claimed in claim 10, wherein the flange comprises a collar on the shank, the collar having an arcuate surface which bears on an arcuate shoulder on the shank whereby the orientation of the collar is automatically adjusted as the collar bears against the bone surface.

12. An outrigger as claimed in claim 10, wherein the threaded portion has an axially extending groove.

13. An outrigger as claimed in claim 10, including an elastomeric bushing provided on the free end of each pin, the pin holding members being clamped about the bushing.

14. In combination, an outrigger for an external fixator and a plurality of transfixing pins for attachment to axially spaced portions of bone, the outrigger comprising first and second pin holding members for attachment to the respective bone portions by means of said pins, each of said pin holding members having a body part with opposite ends and a length dimension extending between said ends, and a connecting means connecting the first and second pin holding members in generally axial alignment, the connecting means including means for adjusting the relative position and orientation of said pin holding members, and said pin holding members each including clamping means for clamping a free end of a transfixing pin in said pin holding member, said pin holding members being spaced apart in said length direction and said transfixing pins extending transversely of said length direction, and the transfixing pins each comprising an elastomeric bushing on the free end of the pin, the pin holding members being clamped about the elastomeric bushing of a pin whereby the pin has limited movement relative to the respective pin holding member, and the other end of the pin being threaded for screwing into a bone portion prior to being clamped by said pin holding member.

* * * * *